(12) United States Patent
Hamisha et al.

(10) Patent No.: US 12,011,577 B2
(45) Date of Patent: Jun. 18, 2024

(54) INJECTION CONFIGURATION WITH MODIFIED LUER CONNECTOR FOR REDUCED DEAD SPACE

(71) Applicant: NanoPass Technologies Ltd., Ness Ziona (IL)

(72) Inventors: Yoav Hamisha, Mazkeret Batya (IL); Gal Admati, Kibbutz Dorot (IL); Yotam Levin, Ness Ziona (IL)

(73) Assignee: NANOPASS TECHNOLOGIES LTD., Ness Ziona (IL)

( * ) Notice: Subject to any disclaimer, the term of this patent is extended or adjusted under 35 U.S.C. 154(b) by 0 days.

(21) Appl. No.: 17/520,899

(22) Filed: Nov. 8, 2021

(65) Prior Publication Data
US 2023/0144090 A1    May 11, 2023

(51) Int. Cl.
*A61M 5/34* (2006.01)
*A61M 5/32* (2006.01)

(52) U.S. Cl.
CPC .............. *A61M 5/34* (2013.01); *A61M 5/329* (2013.01); *A61M 2205/02* (2013.01)

(58) Field of Classification Search
CPC .................... A61M 5/34; A61M 5/329
See application file for complete search history.

(56) References Cited

U.S. PATENT DOCUMENTS

| 2008/0091226 A1* | 4/2008 | Yeshurun | A61M 37/0015 606/186 |
| 2012/0046618 A1* | 2/2012 | Shams | A61M 5/3293 604/241 |
| 2017/0266394 A1* | 9/2017 | Admati | A61M 5/3275 |

* cited by examiner

*Primary Examiner* — Dung T Ulsh
(74) *Attorney, Agent, or Firm* — Rivka Friedman

(57) ABSTRACT

An injection configuration (10) for connection to a male Luer connector (100) includes a hub (12) having an internal conical taper (14) in fluid interconnection with a hollow needle (16). The internal conical taper has a convergence angle of 6% and a length L of 7.5-10.5 millimeters, and presents an entrance aperture diameter D of between 4.365 and 4.595 millimeters.

5 Claims, 2 Drawing Sheets

INJECTION CONFIGURATION WITH MODIFIED LUER CONNECTOR FOR REDUCED DEAD SPACE

FIELD AND BACKGROUND OF THE INVENTION

The present invention relates to needles for use with syringes and, in particular, it concerns an injection configuration having a modified female Luer connector to achieve reduced dead space for dose sparing.

One of the most common configurations for fluid connection between two components throughout a wide range of medical applications is the Luer connector. The connectors have matching male and female conical taper surfaces with an angle of 3.44 degrees (6%) which provide a reliable fluid-tight seal while being easily connected and disconnected. The structure of the connector is fully defined by International Standard ISO 80369.

An analysis of the Luer connector structure as defined by ISO 80369 reveals that the design has an inherent dead space of 40-60 microliters between the end of the male syringe taper and the end of the female Luer taper. In certain applications, particularly where small doses of expensive medications are to be administered, as is common in the case of vaccinations and other biologically active materials, this dead space contributes significantly to wastage and overall costs.

In an attempt to reduce the dead space, U.S. Pat. No. 9,913,949 proposes a shortened female Luer connector, with an overall length of 3-7 mm for the female conical taper, in contrast to the 7.5 mm minimum of the 7.5-10.5 mm range dictated by ISO 80369.

SUMMARY OF THE INVENTION

The present invention is an injection configuration having a modified female Luer connector to achieve reduced dead space for dose sparing.

According to the teachings of an embodiment of the present invention there is provided, an injection configuration for connection to a male Luer connector, the injection configuration comprising: (a) a hub having an internal conical taper having a convergence angle of 6% and a length L of 7.5-10.5 millimeters; and (b) at least one hollow needle configuration in fluid interconnection with the internal conical taper, wherein the internal conical taper has an entrance aperture diameter D of between 4.365 and 4.595 millimeters.

According to a further feature of an embodiment of the present invention, the internal conical taper has an entrance aperture diameter D=L*6%+3.940±0.025 millimeters.

According to a further feature of an embodiment of the present invention, the at least one hollow needle configuration comprises at least one hollow silicon microneedle.

According to a further feature of an embodiment of the present invention, the at least one hollow needle configuration comprises a plurality of hollow silicon microneedles projecting from a major surface of a silicon substrate.

According to a further feature of an embodiment of the present invention, the at least one hollow needle configuration comprises a steel needle.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an injection configuration having a modified female Luer connector to achieve reduced dead space for dose sparing.

The principles and operation of injection configurations according to the present invention may be better understood with reference to the drawings and the accompanying description.

Figure 1:
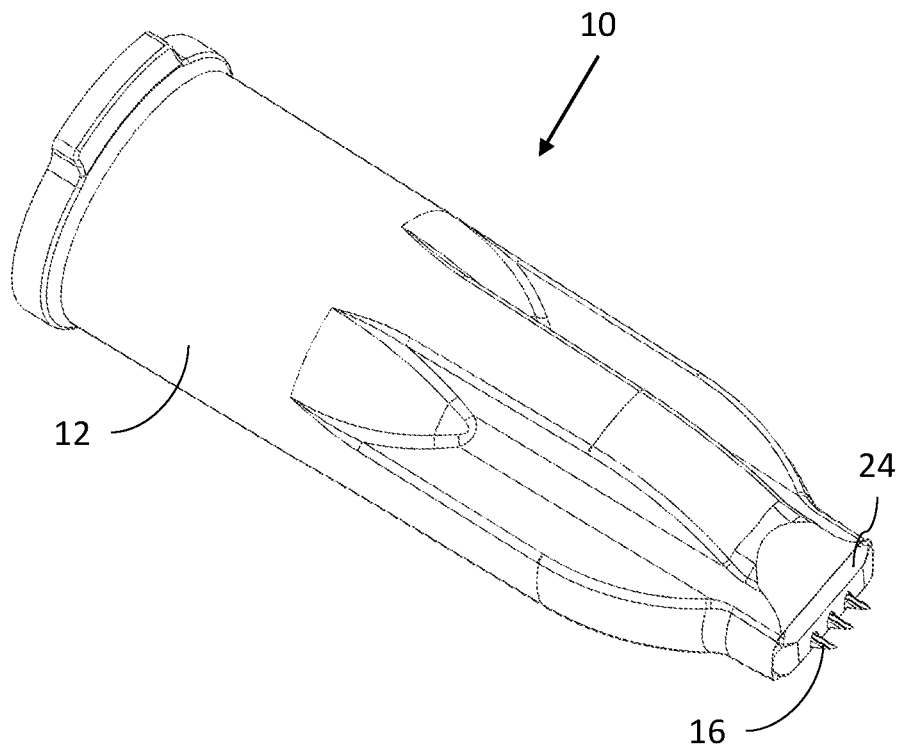
FIG. 1 is an isometric view of an injection configuration constructed and operative according to the teachings of an embodiment of the present invention.
Figure 2:
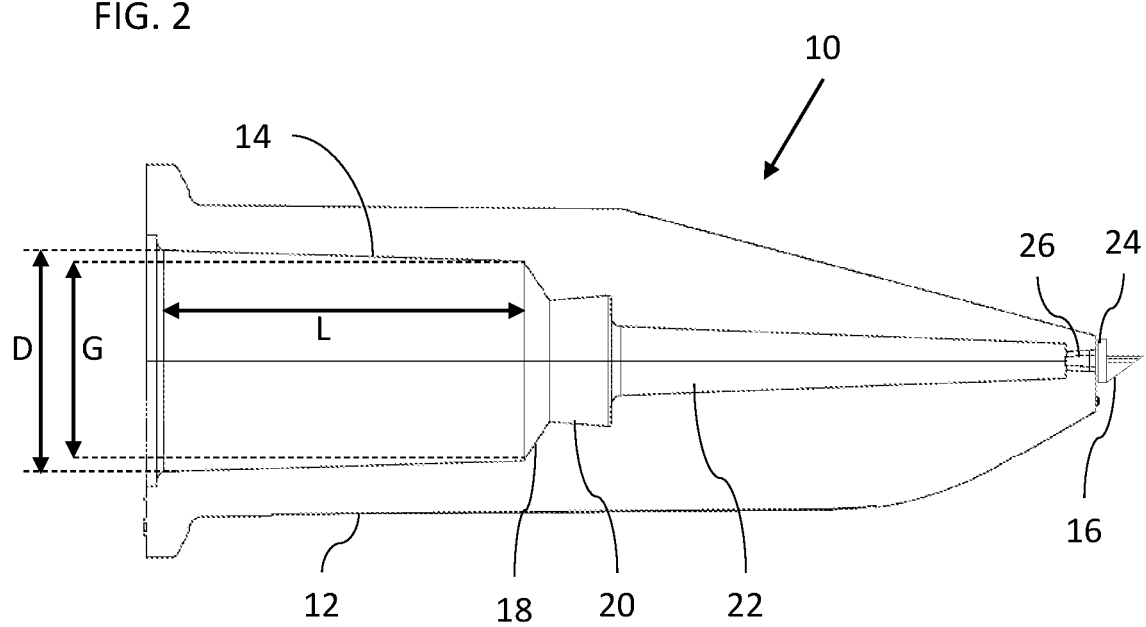
FIG. 2 is a cross-sectional view taken vertically along a central axial plane of the injection configuration of FIG. 1.

Referring now to the drawings, FIGS. 1 and 2 show an injection configuration, generally designated 10, for connection to a male Luer connector. Generally speaking, injection configuration 10 includes a hub 12 having an internal conical taper 14, and at least one hollow needle configuration 16 in fluid interconnection with the internal volume of the internal conical taper.

The internal conical taper 14 has a convergence angle of 6% and a length L of 7.5-10.5 millimeters, such that both the convergence angle and the length conform to standard Luer connector specifications. The internal conical taper is however distinguished from the standard Luer connector specifications by having an entrance aperture diameter D of between 4.365 and 4.595 millimeters.

Most preferably, internal conical taper 14 is implemented with an entrance aperture diameter D given by the formula:

$$D=L*6\%+3.940\pm0.025 \text{ millimeters}$$

where L is the axial length in millimeters of the internal conical taper. It follows that the diameter G of the internal conical taper at the distal end is in the range of 3.940±0.025 millimeters, thereby allowing a standard male Luer connector to reach much closer to the end of the internal conical taper, and thus greatly reducing the dead space within the adapter.

It should be noted that the above references to the entrance diameter and the length of the internal conical taper all relate only to the region which maintains the continuous 6% gradient of the conical surface. In some cases, there is an outwardly-flared region, an outward step and/or an overhanging region of the lateral flange that provides features for engaging with a Luer lock connector, and these may add to the total length of the hub around the entrance to the taper. These areas however are not taken into consideration in the definitions of the entrance aperture and length of the internal conical taper.

Figure 3:
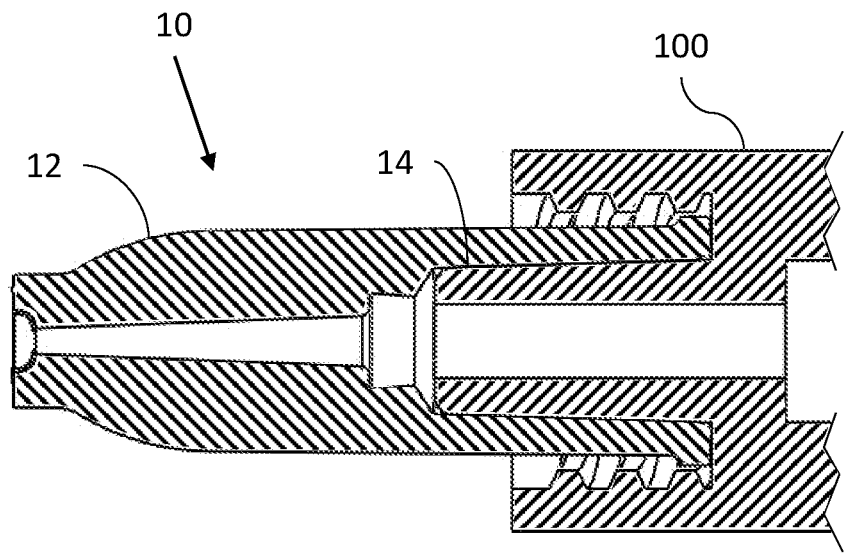
FIG. 3 is a cross-sectional view taken horizontally along a central axial plane of the injection configuration of FIG. 1 showing the engagement of a standard Luer lock male connector with the injection configuration.
Figure 4:
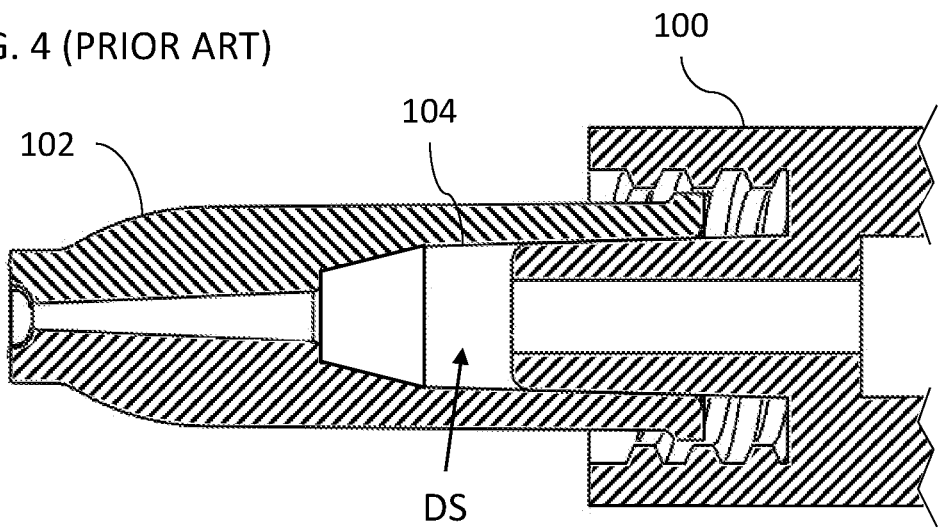
FIG. 4 is a view similar to FIG. 3 showing engagement of standard Luer lock male and female connectors.

The dead space reduction which results from the present invention will be appreciated by comparing FIGS. 3 and 4, which show an inserted position of a standard male Luer connector 100 into hub 12 according to the present invention (FIG. 3) and into a hub 102 with a standard female Luer connector 104 (FIG. 4). As mentioned earlier, the standard Luer connection of FIG. 4 leaves a large dead space DS in the narrow end of the internal conical taper. In contrast, as seen in FIG. 3, the enlarged entrance aperture diameter of hub 12 allows the male Luer connector to penetrate up to very close to the end of the taper, largely eliminating the dead space within the taper. At the same time, by maintaining the overall length of the taper, other mechanical properties of the hub remain similar to those of the standard connector, thereby encouraging the use of the device with industry-standard syringes according to ISO80369. The elongated contact surfaces also provide enhanced retention forces and enhance sealing (reduced risk of leakage) between the syringe and the Luer hub.

Turning now to additional exemplary features of certain preferred embodiments of the present invention as illustrated, a preferred implementation of hub 12 has the following additional features of the internal flow channel beyond the end of the internal conical taper 14. Firstly, a steeply-angled conical region 18 achieves bore diameter reduction from the diameter of the end of the taper to a smaller diameter. In the preferred example illustrated here, this is followed by a small outwardly-sloped taper 20, which provides a feature which has been found useful for extraction of the component from a mold during a plastic injection molding manufacturing process. This is followed by a relatively narrow flow channel 22 which conducts a liquid to the hollow needle configuration.

In one particularly preferred set of implementations, the at least one hollow needle configuration 16 is implemented as at least one, and preferably a plurality, of hollow silicon microneedles. The microneedles are preferably implemented projecting from a major surface of a silicon substrate 24, which is sealingly attached over a liquid distribution channel 26 located at the end of flow channel 22 so as to distribute the liquid for injection to the through bores of each of the microneedles. The term microneedle is used in this context to refer to any sharp structure configured for penetrating into a biological barrier which has a total exposed length no greater than 2 mm, and typically in the range of 300-1500 microns.

Although illustrated herein in a particularly preferred implementation employing microneedles, the at least one hollow needle configuration may equally be a steel needle, rendering the device a direct substitute for a standard needle integrated with a hub for use with a standard Luer lock, or Luer slip, syringe tip.

It will be appreciated that the above descriptions are intended only to serve as examples, and that many other embodiments are possible within the scope of the present invention as defined in the appended claims.

What is claimed is:

1. An injection configuration for connection to a male Luer connector, the injection configuration comprising:
   (a) a hub having an internal conical taper having a convergence angle of 6% and a length L of 7.5-10.5 millimeters; and
   (b) at least one hollow needle configuration in fluid interconnection with said internal conical taper,
wherein said internal conical taper has an entrance aperture diameter D of between 4.365 and 4.595 millimeters, thereby deviating from ISO Standard 80369 for the entrance aperture diameter of a female Luer connector.

2. The injection configuration of claim 1, wherein said internal conical taper has an entrance aperture diameter $D=L*6\%+3.940\pm0.025$ millimeters.

3. The injection configuration of claim 1, wherein said at least one hollow needle configuration comprises at least one hollow silicon microneedle.

4. The injection configuration of claim 1, wherein said at least one hollow needle configuration comprises a plurality of hollow silicon microneedles projecting from a major surface of a silicon substrate.

5. The injection configuration of claim 1, wherein said at least one hollow needle configuration comprises a steel needle.

* * * * *